United States Patent [19]

Harris

[11] Patent Number: 4,850,984
[45] Date of Patent: Jul. 25, 1989

[54] TUBING CONNECTOR

[75] Inventor: Christopher Harris, Oakham, United Kingdom

[73] Assignee: Bard Limited, Sunderland, England

[21] Appl. No.: 3,882

[22] Filed: Jan. 20, 1987

[30] Foreign Application Priority Data

Jan. 17, 1986 [GB] United Kingdom ................ 8601145
Feb. 20, 1986 [GB] United Kingdom ................ 8604175
Mar. 18, 1986 [GB] United Kingdom ................ 8606683

[51] Int. Cl.⁴ ............................................. A61M 1/00
[52] U.S. Cl. .................................. 604/326; 604/283;
285/235; 285/292; 285/417; 285/423; 128/912
[58] Field of Search ................ 604/317, 322, 326, 93,
604/905, 280, 283, 262, 408; 285/260, 308, 332,
423, 235, 292, 398, 417, 418; 128/912

[56] References Cited

U.S. PATENT DOCUMENTS

| 2,117,357 | 5/1938 | Peterson | 285/235 |
| 3,058,472 | 10/1962 | Thornton, Jr. | 604/283 |
| 3,908,635 | 9/1975 | Vick | 604/280 |
| 4,052,990 | 10/1977 | Dodgson | 285/260 |
| 4,238,059 | 12/1980 | Caraway et al. | 285/332 |
| 4,325,387 | 4/1982 | Helfr | 285/235 |
| 4,349,024 | 9/1982 | Ralston, Jr. | 604/905 |
| 4,354,490 | 10/1982 | Rogers | 604/905 |
| 4,641,860 | 2/1987 | McMichle et al. | 285/398 |

FOREIGN PATENT DOCUMENTS

| 8203006 | 9/1982 | PCT Int'l Appl. | 604/317 |
| 405428 | 2/1934 | United Kingdom . | |
| 545717 | 6/1942 | United Kingdom . | |
| 625421 | 6/1949 | United Kingdom . | |
| 768326 | 2/1957 | United Kingdom . | |
| 2091365 | 7/1982 | United Kingdom | 285/423 |

Primary Examiner—C. Fred Rosenbaum
Assistant Examiner—Mario Costantino
Attorney, Agent, or Firm—Dennison, Meserole, Pollack & Scheiner

[57] ABSTRACT

A one-piece connector has a stepped bore, a first end to accommodate an outlet pipe of an outlet tap of a urine drainage leg bag, and a second end to accomodate a nozzle on an inlet pipe of an overnight drainage bag.

The second end includes a hand-grippable tab with an enlarged free end.

The connector is removed from the nozzle by pulling the tab in a direction towards the leg bag. This pulling action on the tab reduces substantially the tension needed to separate the connector from the nozzle.

14 Claims, 2 Drawing Sheets

TUBING CONNECTOR

This invention relates to a device for effecting a temporary connection of a nozzle to a tube or pipe, the device comprising a cylindrical moulded elastomeric connector tube having a first end to accommodate the end of the tube or pipe and a second end to accommodate the nozzle.

Incontinent patients who wear a urine drainage bag on their leg—a so-called "leg bag"—can connect an outlet tube on the leg bag to the inlet tube of a larger bag not carried on their body—a so-called "overnight drainage system".

If a simple length of rubber tubing is used to connect the two bags at night, there are likely to be problems for patients who lack strength or co-ordination in their fingers in separating the two bags in the morning. In any event, separation of the connector and inlet tube is likely to be sudden and at a time when a relatively high force is being applied, which itself is undesirable. Soiling of the hands with urine is highly likely.

To overcome this difficulty, the manufacturers of urine drainage systems have made various proposals for facilitating disconnection. These proposals also have their disadvantages, in that putting them into practice is substantially more expensive than using a length of rubber tubing and, more importantly, limits choice of an overnight drainage system to that which is compatible with the proprietary connector and leg bag used by the patient. Their very complexity may in addition cause confusion in some patients.

It is accordingly an object of the present invention to retain the virtues of simplicity and adaptability of the simple rubber tubing connection, while at the same time making it easy for patients with limited strength in their fingers to separate the overnight drainage system from the connector.

According to the present invention there is provided a device for connecting a nozzle to a tube, said device comprising a cylindrical moulded elastomeric connector tube having two ends, each one of said ends being adopted to accommodate either the nozzle or an end of the tube, and a hand-grippable appendage protruding from an attachment area on the circumference of the exterior cylindrical surface of the connector tube within a terminal zone of one of said tube ends.

In one device of the invention the appendage (otherwise called a "tab") is mounted at the end of the tube which is adapted to accommodate the inlet nozzle of an over night drainage bag.

The invention stems from a recognition that attempts to disconnect the inlet nozzle of the overnight bag from a simple rubber tubing connector are frustrated by the tendency of the rubber tubing, when placed in lengthwise tension, to suffer an increase in hoop tension, with consequent increase of the frictional grip of the tube on the nozzle of the overnight bag.

Pulling on the tab of the connector according to the invention, in a direction towards the leg bag itself, will avoid the longitudinal tension in the connector. Indeed, pulling on the tab may place the connector in longitudinal compression, leading to an increase in its diameter. In any event, pulling on the tab in this way brings about a very substantial reduction in the tension needed to separate the nozzle from the connector. In the experience of the Applicants, the reduction is so large that it can fairly be described as "dramatic". It is certainly surprising and unexpected in its magnitude.

It is important to acceptance of the device that it does not interfere with normal operation of the outlet valve and does not protrude so as to snag on clothing. There is a fortunate conjunction of acceptability and operational efficiency in that the most effective angle of pull is back along the axis of the connector, and arranging the tab to lie along the axis will encourage users to pull in the best direction for disconnection of the nozzle, at the same time reducing snagging to a minimum.

In a modification, which is useful for so-called "community patients", the other end of the tube is fitted to the inlet tube of the overnight bag and the said one end of the tube is fitted temporarily over an outlet spigot of the outlet valve of the leg bag.

In a further modification, the said other end of the tube is also provided with a hand-grippable appendage which protrudes from an attachment area on the circumference of the exterior cylindrical surface of the connector tube, within a terminal zone of the first end of the connector tube.

Preferably the two tube ends are identical to each other, and the two appendages are positioned on the circumference of the tube diametrically opposite to one another.

For a better understanding of the present invention, and to show how clearly how the same may be carried into effect, reference will now be made, by way of example, to the accompanying drawings, in which.

Figure 1:
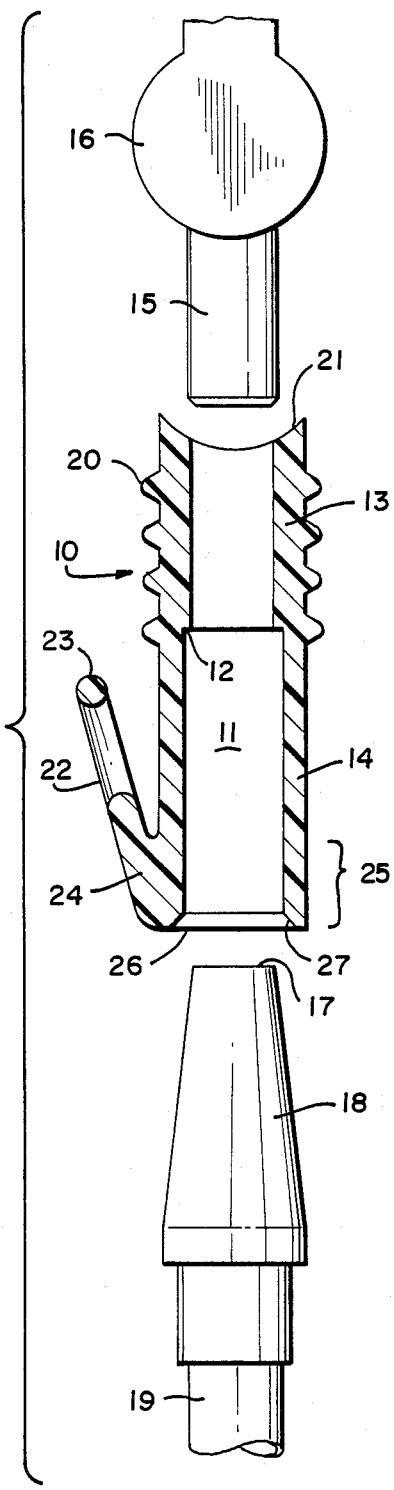
FIG. 1 is an exploded longitudinal diametral view of a first connector in accordance with the invention, the outlet pipe and tap of a leg bag and the nozzle of an overnight bag.
Figure 2:
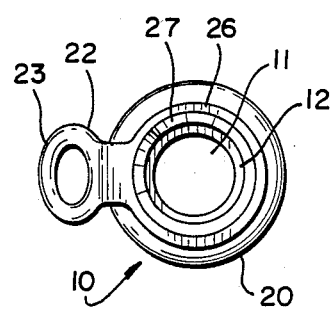
FIG. 2 is a transverse view of the connector from its one end.

Referring to FIGS. 1 and 2 an injection moulded, one-piece connector 10 has a bore 11 with a step 12 which divides the length of the connector 10 into a first end 13 and a second end 14. The bore in the first end accommodates the outlet pipe 15 of an outlet tap 16 of a urine drainage leg bag.

The bore in the second end 14 accommodates the open end 17 of a nozzle 18 on the remote end of an inlet pipe 19 of an overnight drainage bag (not shown). On its first end 13, the external cylindrical surface of the connector 10 carries a number of ribs 20 in the form of hoops, which assist in pushing the connector on to the outlet tube 15 and retaining it thereon. The terminal surface 21 of the first end 13 is arcuate, to accommodate the transverse barrel valve cylinder of the outlet valve 16.

The second end 14 of the connector 10 includes a hand-grippable tab 22 with an enlarged free end 23 to assist gripping. The other, attached end 24 of the tab 22 is contiguous with the second end 14 at its terminal zone 25. The end surface 26 of the first end 14 is chamfered at 27 to facilitate insertion of the nozzle 18.

The connector is made typically of silicone rubber, of a mid-range hardness (42 or 43 Shore A). The internal diameter of the second end of the connector is 8.5 mm which, with the stated material, gives sufficient flexibility to accept a wide variety of overnight bag nozzles in current use. The tab 22 is essentially planar, its plane lying at an angle of 15° to the longitudinal axis of the connector 10. Thus, the tab does not protrude enough to be inconvenient, and serves to encourage users to pull it in the most effective direction, that is, back towards the outlet valve 16. It has been found important to ensure that the point of attachment of the tab 22 on the external cylindrical surface of the connector 10 is as close as possible to the end surface 26 of the second end 14 of the connector.

In use, the tab 22 is gripped in one hand and the tube 19 or nozzle 18 in the other, and the hands then pulled apart. In separation there is less likelihood than with a simple rubber tube connector that the hands will be soiled with urine.

Other connector device materials (e.g. latex) and tab shapes are possible. In particular, the distal end 23 of the tab 22 could incorporate a ring-shape, to make pulling of the tab even easier.

The outlet valve 16 is described in greater detail in GB-A-2129912. It is envisaged that the present connector would be "factory-fitted" to the outlet valve of a leg bag, e.g. the outlet valve 16.

The nozzle 18 of the overnight bag is usually a catheter connector adapted to engage with the funnel end of a urinary drainage catheter.

Other designs of outlet tap have a shape totally different from the one illustrated. Connectors to co-operate with them will have a first end of correspondingly different shape.

The tab may incorporate indicia to suggest correct operation, for example, an arrow shape moulded in relief into the outward-facing flat surface of the illustrated tab.

Figure 3:
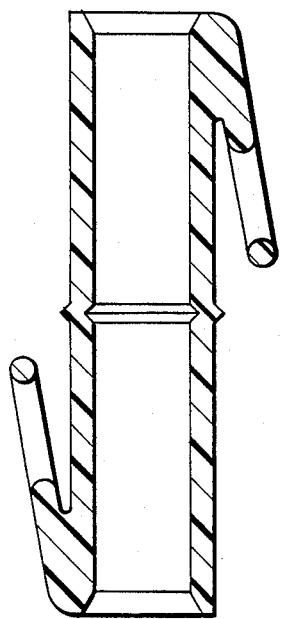
FIG. 3 is a diametral longitudinal section of a section connector in accordance with the invention.

FIG. 3 illustrates a modified tubing connector device having hand-grippable appendages at both ends.

Such a connector could be factory-fitted to the inlet tube of an "overnight" or "bedside" urine drainage bag, and preferably to the usual rigid and tapered element provided on the inlet end of the inlet tube for its connection to a urinary drainage catheter. The connector affords easy connection to the inlet tube to the outlet of a urine drainage bag worn on the leg of the user (leg bag), and disconnection from the leg bag.

If the user desires, he can break the connection at the junction of the connector and the inlet tube of the overnight bag, leaving the connector on his leg bag outlet, simply by pulling on the inlet tube and the tab of the connector adjacent the inlet tube. Even if the connector is normally left on the inlet tube of the overnight bag, it can be readily removed whenever the inlet tube has to be connected to a sheath or urinary drainage catheter.

Adaptability of the connector to suit the different needs of a multitude of individual users is an important consideration governing acceptance of the device by users and health care organisations. Ease of use, especially by infirm or handicapped users, is necessary, as is design simplicity and a low manufacturing cost. The proposed device meets all these requirements.

This connector is also made typically of silicone rubber of a mid-range hardness (42 or 43 Shore A). The two tabs have the same construction and positioning as the tab 22 of the connector illustrated in FIGS. 1 and 2. It is to be understood however that with the connector illustrated in FIG. 3, other materials such as latex and tab shapes can be used.

I claim:

1. A device for connecting a nozzle to a tube, said device comprising a cylindrical molded elastomeric connector tube having two ends, each one of said ends being adapted to accommodate either the nozzle or an end of the tube, an attachment area on the circumference of the exterior cylindrical surface of the connector tube at a terminal zone of one of said tube ends, and a hand-gripped elongate appendage protruding from said attachment area toward the other of said tube ends at an acute angle to the longitudinal axis of the connector tube, said elongate appendage comprising means for reducing the tension needed to separate the connector from the nozzle or tube when the appendage is pulled towards said other end.

2. A device as claimed in claim 1 in which the appendage has an enlarged free end to assist gripping.

3. A device as claimed in claim 1 in which the free end of the appendage includes a ring-shaped member to assist gripping.

4. A device as claimed in claim 1 in which the appendage is contiguous with the said one end of the tube at the terminal zone.

5. A device as claimed in claim 1 in which the appendage is essentially planar.

6. A device as claimed in claim 5 in which the appendage protrudes at an angle of approximately 15° to the longitudinal axis of the tube.

7. A device as claimed in claim 1 further including a second hand-grippable appendage protruding from an attachment area on the circumference of the exterior cylindrical surface of the connector tube within a terminal zone of the other of said tube end.

8. A device as claimed in claim 7 in which said appendages are diametrically opposite one another.

9. A device as claimed in claim 7 in which said appendages are substantially identical to one another.

10. A device as claimed in claim 7 in which the two tube ends are substantially identical to one another.

11. A device as claimed in claim 1 further including ribs located on the exterior surface of the connector tube in the region of the other of said tube ends.

12. A device as claimed in claim 1 made of silicone rubber of a mid-range hardness (42 or 43 Shore A).

13. A device as claimed in claim 1 which is made of latex.

14. A device as claimed in claim 1 in which the internal diameter of said one end is 8.5 mm.

* * * * *